United States Patent [19]
Siman et al.

[11] Patent Number: 6,048,703
[45] Date of Patent: Apr. 11, 2000

[54] METHODS FOR DETECTING CELL APOPTOSIS

[75] Inventors: Robert Siman, Wilmington, Del.; Donna Bozyczko-Coyne, Landenberg, Pa.; Sheryl L. Meyer, Collegeville, Pa.; Ratan Venkatraman Bhat, West Chester, Pa.

[73] Assignee: Cephalon, Inc., West Chester, Pa.

[21] Appl. No.: 08/967,625

[22] Filed: Nov. 12, 1997

Related U.S. Application Data

[60] Provisional application No. 60/030,961, Nov. 15, 1996.

[51] Int. Cl.$^7$ ........................ G01N 33/53; G01N 33/567; G01N 33/536; C07K 16/00
[52] U.S. Cl. ........................ 435/7.1; 435/7.22; 435/7.21; 435/7.23; 435/7.24; 435/7.9; 435/7.92; 435/7.93; 435/7.94; 435/7.95; 436/501; 436/503; 436/504; 436/515; 436/536; 436/544; 436/545; 436/546; 530/387.9
[58] Field of Search ........................ 435/7.21, 7.9, 435/7.92, 7.93, 7.94, 7.95, 7.1, 7.22, 7.23, 7.24; 530/387.9; 436/501, 503, 504, 515, 536, 544, 545, 546

[56] References Cited

U.S. PATENT DOCUMENTS

| | | | |
|---|---|---|---|
| 5,536,639 | 7/1996 | Siman et al. | 435/7.1 |
| 5,605,826 | 2/1997 | Wright eet al. | 435/226 |

OTHER PUBLICATIONS

Amendola et al Proc. Natl. Acad. Sci. vol. 93, (20) pp. 11057–62, Oct. 1, 1996.

Catty et al Antibodies vol. II Ed by D. Catty (1989) IRL Press pp. 97–154, 1989.

Harlow et al Antibodies Ed by Harlow & Lane CSHL Press Ch 12–pp. 473–510, 1988.

Alnenui et al., "Cloning and Expression of Four Novel Isoforms of Human Interleukin–1β Converting Enzyme with Different Apoptotic Activities", *J. Biol. Chem.*, 1995, 270(9), 4312–4317.

Batistatou et al., "Bcl–2 Affects Survival but Not Neuronal Differentiation of PC12 Cells", *J. Neurosci.*, 1993, 13(10), 4422–4428.

Cherney et al., "cDNA sequence, protein structure, and chromosomal location of the human gene for poly (ADP–ribose) polymerase", *Proc. Natl. Acad. Sci. USA*, 1987, 84, 8370–8374.

Cohen et al., "Key morphological features of apoptosis may occur in the absence of internucleosomal DNA fragmentation", *Biochem. J.*, 1992, 286, 331–334.

Collins et al., "Continuous growth and differentiation of human myeloid leukaemic cells in suspension culture", *Nature*, 1977, 270, 347–349.

Crompton et al., "Propidium iodide staining correlates with the extent of DNA degradation in isolated nuclei", *Biochem. Biophys. Res. Commun.*, 1992, 183(2), 532–537.

Duan et al., "ICE–LAP6, a Novel Member of the ICE/Ced–3 Gene Family, Is Activated by the Cytotoxic T Cell Protease Granzyme B", *J. Biol. Chem,*, 1996, 271, (28) 16720–16724.

Enari et al., "Involvement of an ICE–lik protease in Fas–mediated apoptosis", *Nature*, 1995, 375, 78–81.

Faucheu et al., "A novel human protease similar to the interleukin–1β converting enzyme induces apoptosis in transfected cells", *EMBO J.*, 1995, 14(9), 1914–1922.

Enari et al., "Sequential activation of ICE–like and CPP32–like proteases during Fas–mediated apoptosis", *Nature*, 1996, 380, 723–726.

Fernandes–Alnemri et al., "CPP32, a Novel Human Apoptotic Protein with Homology to *Caenorhabditis elegans* Cell Death Protein Ced–3 and Mammalian Interleukin–1β–converting Enzyme", *J. Biol. Chem.*, 1994, 269(49), 30761–30764.

Fernandes–Alnemri et al., "Mch2, a New Member of the Apoptotic Ced–3/Ice Cysteine Protease Gene Family", *Cancer Res.*, 1995, 55, 2737–2742.

Frey, "Nucleic Acid Dyes for Detection of Apoptosis in Live Cells", *Cytometry*, 1995, 21, 265–274.

Gagliardini et al., "Prevention of Vertebrate Neuronal Death by the *crmA* Gene", *Science*, 1994, 263, 826–828.

Gavrieli et al., "Identification of Programmed Cell Death In Situ via Specific Labeling of Nuclear DNA Fragmentation", *J. Cell Biol.*, 1992, 119(3), 493–501.

Gu et al., "Cleavage of Poly(ADP–ribose) Polymerase by Interleukin–1β Converting Enzyme and Its Homologs TX and Nedd–2", *J. Biol. Chem.*, 1995, 270(32), 18715–18718.

Hoeppner et al., "Programmed cell death: from development to disease", *Biochim. Biophys. Acta*, 1966, 1242, 217–220.

Huppi et al., "Sequence and organization of the mouse poly (ADP–ribose) polymerase gene", *Nucl. Acids. Res.*, 1989, 17(9), 3387–3401.

Ittel et al., "Chicken poly(ADP–ribose) synthetase: complete deduced amino acid sequence and comparison with mammalian enzyme sequences", *Gene*, 1991, 102, 157–164.

Kamens et al., "Identification and Characterization of ICH–2, a Novel Member of the Interleukin–β–converting Enzyme Family of Cysteine Protease", *J. Biol. Chem.*, 1995, 270(25), 15250–15256.

Fernandez–Alnemri et al., "Mch3, a Novel Human Apoptotic Cysteine Protease Highly Related to CCP32", *Cancer Res.*, 1995, 55, 6045–6052.

(List continued on next page.)

*Primary Examiner*—Sheela Huff
*Assistant Examiner*—Geetha P. Bansal
*Attorney, Agent, or Firm*—Fish & Richardson P.C.

[57] ABSTRACT

Methods for the biochemical and immunohistochemical detection of cell apoptosis are described. The methods utilize the detection and measurement of polypeptide fragments generated during apoptosis. Conditions associated with apoptosis may be detected by the methods of this invention. Methods are also presented for the screening of potential therapeutic compounds which inhibit or stimulate apoptosis. Kits for detection of apoptosis and diagnosis of diseases are also provided.

4 Claims, 7 Drawing Sheets

OTHER PUBLICATIONS

Kaufmann et al., "Specific Proteolytic Cleavage of Poly (ADP–ribose) Polymerase: An Early Marker of Chemotherapy–induced Apoptosis", *Cancer Res.*, 1993, 53, 3976–3985.

Lamarre et al., "Production and characterization of monoclonal antibodies specific for the functional domains of poly (ADP–ribose) polymerase", *Biochem. Cell Biol.*, 1986, 64, 368–376.

Lassmann et al., "Cell death in Alzheimer's disease evaluated by DNA fragmentation in situ", *Acta. Neuropathol.*, 1995, 89, 35–41.

Lazebnik et al., "Cleavage of poly(ADP–ribose) polymerase by a proteinase with properties like ICE", *Nature*, 1994, 371, 346–347.

Lippke et al., "Identification and Characterization of CPP32/Mch2 Homolog 1, a Novel Cysteine Protease Similar to CPP32", *J. Biol. Chem.*, 1996, 271, (4), 1825–1828.

Los et al., "Requirement of an ICE/CED–3 protease for Fas/APO–1–medicated apoptosis", *Nature*, 1995, 375, 81–83.

Malik et al., "Antibody to poly(adenosine diphosphate–ribose) polymerase and its use in chromatin analysis", *Nucl. Acid Res.*, 1982, 10(9), 2939–2950.

Martin et al., "Protease Activation during Apoptosis: Death by a Thousand Cuts?", *Cell*, 1995, 82, 349–352.

Meyer et al., "Enzymatic Properties of Recombiant ICH–1L Support a Role in Mediating Apoptosis", *Soc. Neurosci.*, 1996, 22, 565, Abstract No. 228.3.

Milligan et al., "Peptide Inhibitors of the ICE Protease Family Arrest Programmed Cell Death of Motoneurons In Vivo and Vitro", *Neuron*, 1995, 15, 385–393.

Miura et al., "Introduction of Apoptosis in Fibroblasts by IL–1β–Converting Enzyme, a Mammalian Homolog of the C. elegans Cell Death Gene ced–3", *Cell*, 1993, 75, 653–660.

Muzio et al., "Flice, A Novel FADD–Homologous ICE/CED–3–like Protease, is Recruited to the CD95 (Fas/APO–1) Death–Inducing Signaling Complex", *Cell*, 1996, 85, 817–827.

Nicholson et al., "Identification and inhibition of the ICE/CED–3 protease necessary for mammalian apoptosis", *Nature*, 1995, 376, 37–43.

Nicoletti et al., "A rapid and simple method for measuring thymocyte apoptosis by propidium iodide staining and flow cytometry", *J. Immunol. Methods*, 1991, 139, 271–279.

Nitatori et al., "Delayed Neuronal Death in the CA1 Pyramidal Cell Layer of the Gerbil Hippocampus following Transient Ischemia is Apoptosis", *J. Neurosci.*, 1995, 15(2), 1001–1011.

Oppenheim, "Cell Death During Development of the Nervous System", *Annu. Rev. Neurosci.*, 1991, 14, 453–501.

Roberts–Lewis et al., "Immunolocalization of Calpain I–mediated Spectrin Degradation to Vulnerable Neurons in the Ischemic Gerbil Brain", *J. Neurosci.*, 1994, 14(6), 3934–3944.

Saito et al., "Cloning of a full–length cDNA encoding bovine thymus poly(ADP–ribose) synthetase: evolutionarily conserved segments and their potential functions", *Gene*, 1990, 90, 249–254.

Schlegel et al., "CPP32/Apopain Is a Key Interleukin 1β Converting Enzyme–like Protease Involved in Fas–mediated Apoptosis", *J. Biol. Chem.*, 1996, 271(4), 1841–1844.

Schulze–Osthoff et al., "Cell Nucleus and DNA Fragmentation Are Not Required for Apoptosis", *J. Cell Biol.*, 1994, 127(1), 15–20.

Shah et al., "Detection of Poly(ADP–Ribose) Polymerase and Its Apoptosis–Specific Fragment by a Nonisotopic Activity–Western Blot Technique", *Analyt. Biochem.*, 1995, 232, 251–254.

Tewari et al., "Yama/CPP32β, a Mammalian Homolog of CED–3, Is a CrmA–Inhibitable Protease That Cleaves the Death Substrate Poly (ADP–Ribose) Polymerase", *Cell*, 1995, 81, 801–809.

Thompson, "Apoptosis in the Pathogenesis and Treatment of Disease", *Science*, 1995, 267, 1456–1462.

Troy et al., "The contrasting roles of ICE family proteases and interleukin–1β in apoptosis induced by trophic factor withdrawal and copper/zinc superoxide dismutase down–regulation", *Proc. Natl. Acad. Sci. USA*, 1996, 93, 5635–5640.

Wang et al., "Ich–1, an ICE/ced–3–Related Gene, Encodes Both Positive and Negative Regulators of Programmed Cell Death", *Cell*, 1994, 78, 739–750.

Wijsman et al., "A New Method to Detect Apoptosis in Paraffin Sections: In Situ End–labeling of Fragmented DNA", *J. Histochem. Cytochem.*, 1993, 41(1), 7–12.

Woo, "Apoptosis and Loss of Renal Tissue in Polycystic Kidney Diseases", *N. Engl. J. Med.*, 1995, 333, 18–25.

Wood et al., "In Situ Labeling of Granule Cells for Apoptosis–Associated DNA Fragmentation Reveals Different Mechanisms of Cell Loss in Developing Cerebellum", *Neuron*, 1993, 11, 621–632.

Wyllie, "Glucocorticoid–induced thymocyte apoptosis is associated with endogenous endonuclease activation", *Nature*, 1980, 284, 555–556.

Wyllie et al., "Chromatin Cleavage in Apoptosis: Association with Condensed Chromatin Morphology and Dependence on Macromolecular Synthesis", *J. Pathol.*, 1984, 142, 67–77.

Zhivotovsky et al., "Multiple Proteases are Involved in Thymocyte Apoptosis", *Exp. Cell Res.*, 1995, 221, 404–412.

FIG. 2
FIG. 3
FIG. 4

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 5 amino acids
      (B) TYPE: amino acid
      (D) TOPOLOGY: linear (xi) SEQUENCE DESCRIPTION: SEQ ID NO:1:

Gly Asp Glu Val Asp
1           5

(2) INFORMATION FOR SEQ ID NO:2:

-continued

```
    (i) SEQUENCE CHARACTERISTICS:
         (A) LENGTH: 7 amino acids
         (B) TYPE: amino acid
         (D) TOPOLOGY: linear (xi) SEQUENCE DESCRIPTION: SEQ ID NO:2:

Cys Lys Gly Asp Glu Val Asp
1               5
```

METHODS FOR DETECTING CELL APOPTOSIS

CROSS-REFERENCE TO RELATED APPLICATIONS

This patent application claims priority under 35 U.S.C. § 119(e) to provisional patent application Ser. No. 60/030,961, filed Nov. 15, 1996, hereby incorporated in its entirety by reference.

FIELD OF THE INVENTION

The present invention is directed to the detection and quantification of cell apoptosis. More particularly, the present invention is directed to the detection of cell apoptosis by using specific antibodies to detect cells undergoing apoptosis and cells which have undergone apoptotic cell death.

BACKGROUND OF THE INVENTION

Apoptosis is a physiological mechanism of cell death which involves the fragmentation of a cell into membrane-bound particles. The process of apoptosis is involved in a variety of normal and pathogenic biological events, both during development and in adulthood. Agents which affect apoptosis may have therapeutic utility in treating diseases and disorders characterized by aberrant cell proliferation or death (reviewed in Hoeppner et al., Biochim. Biophys. Acta 1242: 217–220, 1966; Thompson, Science 267:1456–1462, 1995). Techniques for detection of apoptosis may be useful to screen for potential therapeutic agents that may induce or prevent apoptosis.

In view of the biological importance of apoptosis, there exists a need for methods to specifically detect cells undergoing apoptosis and those which have suffered apoptotic cell death. These methods are crucial to the identification, characterization, and diagnosis of diseases distinguished by abnormal apoptosis, and to the screening of potential therapeutic agents that may induce or prevent apoptosis.

Several methods are known for the detection of apoptosis in vitro and in vivo, but these have significant drawbacks which limit their utility. Commonly, apoptosis is characterized by condensation and margination of nuclear chromatin, and fragmentation of nuclear structure into so-called apoptotic bodies. This apoptotic morphology can be observed using conventional stains, dyes which selectively accumulate in nuclei such as propidium iodide or Hoechst 33258, or by electron microscopy (e.g., Nicoletti et al., J. Immunol. Methods 139:271–279 1991; Crompton et al., Biochem. Biophys. Res. Commun. 183:532–537 1992; Frey, Cytometry 21:265–274 1995; Woo, N. Engl. J. Med. 333:18–25 1995). Unfortunately, these techniques are either of insufficient specificity or are too laborious and technically complex for the routine selective identification and quantification of apoptotic cells in situ.

Recent attempts to identify and quantify apoptosis have taken advantage of the internucleosomal fragmentation of DNA which is often linked to, but is not diagnostic for, cell death by apoptosis. Various in situ histochemical techniques have been applied to the end-labeling of nicked DNA (Gavrieli et al., J. Cell Biol. 119:493–501 1992; Wijsman et al., J. Histochem. Cytochem. 41:7–12 1993; Wood et al., Neuron 11:621–632 1993). Although these techniques have become popular for marking apoptotic cells in situ, it has become recognized recently that DNA fragmentation can also result from cell stress or necrotic degeneration. Consequently, the in situ techniques which detect fragmented DNA are not selective in detecting cells undergoing apoptosis (Nitatori et al., J, Neurosci. 15:1001–1011 1995; Lassmann et al., Acta Neuropathol, 89:35–41 1995).

Molecular techniques have also been employed for the detection in cell and tissue extracts of internucleosomal DNA degradation linked to apoptosis (Wyllie, AH, Nature 284:555–556 (1980); Wyllie et al., J. Pathol. 142:67–77 (1984)). The in situ and molecular techniques which rely on the detection of internucleosomal DNA fragmentation are not sufficiently thorough for the detection of apoptotic cell death since they do not detect forms of apoptosis not associated with internucleosomal DNA degradation (Cohen et al., Biochem. J. 286:331–334 1992; Schulze-Osthoff et al., J. Cell Biol. 127:15–20 1994). Moreover, the molecular methods lack the sensitivity and cellular resolution needed to define the role of apoptosis of particular cell types in disease processes. This is especially true for chronic slow degenerative diseases, in which cell death is protracted and asynchronous, and individual apoptotic cells are present for only a limited period of time.

An increased understanding of the biochemical mechanisms of apoptotic cell death has arisen from recent genetic and cell biological studies. A family of cysteine proteases related to interleukin-1β converting enzyme (ICE) has been found to play an essential role in the intracellular pathway of apoptosis (reviewed in Martin et al., Cell 82:349–352 1995). ICE itself is not a mediator of apoptosis in most mammalian cell types. Rather, a family of homologous proteases comprising at least nine human ICE family proteases have been identified to date (ICE, CPP32/apopain/Yama, ICH-1, TX/ICH-2/ICE$_{rel}$III, ICE$_{rel}$III, MH-1/MH-3/ICE-LAP3, Mch2, FLICE/Mch5, ICE-LAP6/Mch6), each of which leads to apoptosis when over-expressed in a proteolytically active form in cultured mammalian cells (Miura et al., Cell 75:653–660 1993; Wang et al., Cell 78:739–750 1994; Fernandes-Alnemri et al., J. Biol. Chem. 269:30761–30764 1994—Faucheu et al., EMBO J. 14:1914–22 (1995); Kamens et al., J. Biol. Chem, 270:15250–15256 1995, Alnenui et al., J. Biol. Chem. 270:4312–4317 1995; Fernandes-Alnemri et al., Cancer Res. 55:6045–6052 1995; Lippke et al., J. Biol. Chem. 271:1825–1828 1996; Muzio et al., Cell 85:817–827 1996; Duan et al., J. Biol. Chem. 271:16720–16724 1996). Moreover, treatment of cells with apoptotic stimuli increases ICE-like proteolytic activity in cell extracts (Los et al., Nature 375:81–83 1995; Enari et al., Nature 380:723–726 1996). Proteolytic activity by ICE homologues is required to initiate apoptosis, since overexpression of mutant, inactive ICE homologues does not lead to apoptosis, and several protease inhibitors of the ICE family block apoptosis (Miura et al., ibid.; Gagliardini et al., Science 263:826–828 1994; Enari et al., Nature 375:78–81 1995; Milligan et al,, Neuron 15:385–393 1995, Los et al., ibid.; Zhivotovsky et al., Exp. Cell Res. 221:404–412 1995; Schlegel et al., J. Biol. Chem. 271:1841–1844 1996).

Degradation of specific cellular proteins, as would be expected to occur following the activation of an ICE-like protease, has also been associated with apoptosis. For example, poly(ADP-ribose)polymerase (PARP) is cleaved specifically during apoptosis in mammalian cells (Kaufmann et al., Cancer Res, 53:3976–3985 1993) and is an excellent substrate in vitro for several ICE homologues (Tewari et al., Cell 81:801–809, 1995; Nicholson et al., Nature 376:37–43 1995; Gu et al., J. Biol. Chem. 270:18715–18718, 1995; Fernandes-Alnemri et al., Cancer Res. 55:2737–2742 1995-, Fernandes-Alnemri et al., ibid.; Lippke et al., J. Biol. Chem. 271:1825–1828 1996). In the human promyelocytic leukemia cell line HL60 (Collins et al,, Nature 270:347–349 1977), PARP is degraded in response to incubation with etoposide, which leads to cell death by apoptosis (Kaufmann et al., ibid). Protease inhibitors which block the activity of ICE homologues prevent not only apoptosis, but PARP degradation as well (Schlegel et al., ibid.).

Due to the inadequacies in many of the known methods for the detection of cell apoptosis, there continues to be a need for new, selective methods of detection. The present invention is directed to this, as well as other, important ends.

SUMMARY OF THE INVENTION

The present invention provides methods for the biochemical and histochemical detection of apoptosis. The methods are based on the use of antibodies which react selectively with fragments of proteins whose degradation is stimulated during apoptosis.

In one embodiment, there is provided a method of detecting apoptosis by using antibodies which bind specifically to peptides or fragments of proteins having the COOH-terminal amino acid sequence SEQ ID NO: 1 (GDEVD) which are generated during apoptosis. The method involves contacting a sample of cells with the antibody, and determining by immunoassay the amount of the antibody which binds to the sample relative to the amount of antibody which binds to a sample known to be free of apoptosis.

Another embodiment provides a method of detecting apoptosis in situ based on the use of immunohistochemical staining of cells in a fixed preparation. The preparation may be a culture of cells which have been fixed or a sample of tissue fixed and sectioned. The fixed preparation is contacted with an antibody prepared against the peptide sequence of SEQ ID NO:2 (CKGDEVD).

In another embodiment of the invention, a first sample of cells containing a protein which generates immunoreactive fragments during apoptosis is exposed to a test compound under conditions or treatment known to trigger apoptosis in the cells. A second sample of the same cells is also placed under conditions known to trigger apoptosis, in the absence of any test compound. A test compound inhibits apoptosis if antibody binding to the first sample is less than antibody binding to the second sample.

In still another embodiment, a first sample of cells is exposed to a test compound. A second sample of the same cells is not exposed to the test compound. A test compound stimulates apoptosis if antibody binding to the first sample is greater than antibody binding to the second sample.

In another embodiment, a candidate compound is administered to a mammal, preferably a rodent such as, for example, a gerbil, mouse, or rat, under conditions known to stimulate apoptosis. The level of apoptosis-generated protein fragments is determined using immunoassays as described above. A compound tests positive as an inhibitor of apoptosis if the amount of apoptosis-generated protein fragments taken from an animal to which the candidate compound had been administered is less than that present in an equivalent sample from an animal exposed to the same apoptosis-stimulating conditions, but not exposed to the candidate compound.

In yet another embodiment, a candidate compound is administered to a mammal, such as a gerbil, mouse, or rat, and the level of apoptosis-generated protein fragments is determined using immunoassays as described above. A compound tests positive as a stimulator of apoptosis if the amount of apoptosis-generated protein fragments taken from an animal to which the candidate compound had been administered is greater than that present in an equivalent sample from an animal not exposed to the candidate compound.

Another embodiment of the present invention is the detection in a subject of disease, disorder, or condition associated with cell apoptosis. A sample of cells is obtained from the subject. The sample is contacted with an antibody against SEQ ID NO:2. The extent of binding of the antibody with cells in the sample is determined, preferably by immunoassay, relative to a control sample known to be free of apoptosis.

Another embodiment of the present invention is an antibody prepared against the peptide SEQ ID NO:2 (CKGDEVD). The antibody preferably reacts selectively with the about 30 kDa $NH_2$-terminal polypeptide derivative of poly(ADP-ribose)polymerase produced in cells undergoing apoptosis.

Another embodiment of the present invention is a kit for in vitro determination of the level of apoptosis-generated protein fragments in a sample. The kit comprises: (1) a primary antibody capable of binding to protein fragments generated during apoptosis, (2) a secondary antibody conjugated to a signal-producing label, the secondary antibody being one which binds to the primary antibody; alternatively, the secondary antibody binds specifically to an apoptosis-generated protein fragment at an epitope different from that to which the primary antibody binds; and (3) a signal-producing tertiary reagent capable of recognizing a tagged secondary antibody.

BRIEF DESCRIPTION OF THE DRAWINGS

For the purpose of illustrating embodiments of the present invention, there are shown in the drawings certain features. It should be understood, however, that this invention is not limited to the precise embodiments shown.

FIG. 2 shows an immunoblot detection of apoptotic proteolysis in etoposide-treated HL60 cells. Lane 1—untreated cells; Lane 2—two hour etoposide treatment; Lane 3—four hour etoposide treatment. Nuclear extracts prepared from the cells were separated by SDS-PAGE (15 μg protein per lane) and transferred to nitrocellulose by Western blotting. Polypeptides immunoreactive with Ab127 (1/5,000) were labeled by standard techniques (e.g., Harlow and Lane (1988) ibid; Roberts-Lewis et al. (1994) ibid). Note that etoposide-treated apoptotic HL60 extracts, but not extracts from untreated cells, contain an immunoreactive polypeptide of about 30 kDa (arrow), the size expected of the $NH_2$-terminal fragment of PARP (Lazebnik et al. (1994) ibid.) Levels of an immunoreactive polypeptide of approximately 80 kDa also were reproducibly increased in apoptotic cells, whereas faint immunolabeling of an approximately 100 kDa polypeptide was observed regardless of cell treatment.

FIG. 3 represents confirmation that the about 30 kDa immunoreactive polypeptide is labeled by Ab127 and is a protein fragment generated during apoptosis. Nuclear extracts (10 μg per lane) were prepared from etoposide-treated apoptotic HL60 cells (lanes 1,3) or untreated cells (lanes 2,4). Extracts from cells not treated with the etoposide were incubated 15 minutes at room temperature with the ICE-like protease recombinant human caspase 3 (rhCPP32). Lanes 1,2—immunolabeled with Ab127 as described for FIG. 2. Lanes 3,4—immunolabeled with Ab127 that had been preabsorbed with 1.5 µg peptide immunogen (CKGDEVD—SEQ ID NO: 2) per µl antiserum. Note that the immunoreactive about 30 kDa polypeptide in apoptotic cells is also generated by rhCPP32 treatment of a cell extract not treated with etoposide (compare lanes 1 and 2). The immunoreactivity is not observed following preabsorption of the antisense with peptide immunogen (lanes 3, 4).

FIG. 4 shows immunoblot detection of apoptotic proteolysis in growth factor-deprived neuronally differentiated PC12 cells. NGF-differentiated PC12 cells were either maintained (+NGF) or withdrawn (−NGF) from growth factor for 24 hours. Nuclear extracts of differentiated PC12 cells (NUC) were incubated with recombinant CPP32 for either 0, 10, or 40 minutes at room temperature. For comparison, a nuclear extract of HL60 cells that had been incubated with CPP32 is also shown. Note that a strong immunoreactive polypeptide of approximately 46 kDa (and a weak one of approximately 35 kDa, not shown in this figure) is detected in NGF-deprived, but not NGF-maintained, PC12 cells. Immunoreactive polypeptides of identical size are formed in PC12 nuclear extracts incubated with recombinant CPP32. The immunoreactive polypeptides are not derived from PARP, since they migrate differentially from the about 30 kDa PARP fragment apparent in the HL60 extract.

DETAILED DESCRIPTION OF THE INVENTION

Figure 1:
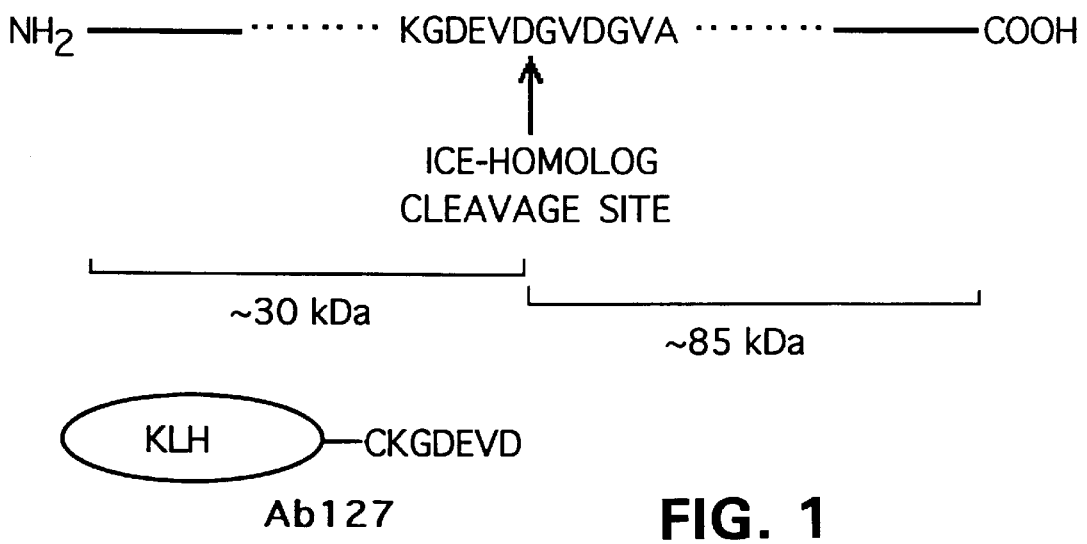
FIG. 1 shows a design of an antibody which reacts selectively with protein fragments generated during apoptosis. The sequence around the site within poly(ADP-ribose) polymerase (PARP) that is cleaved in apoptotic cells is shown at the arrow. The antibodies were designed to react with the COOH-terminal domain of the $NH_2$ terminal fragment of PARP, and other polypeptides carrying the preferred sequence at their carboxy terminus following cleavage.

As employed above and throughout the disclosure, the following terms, unless otherwise indicated, shall be understood to have the following meanings.

"Apoptosis" refers to a specific morphological form of cell death characterized by fragmentation of cells and their nucleii into membrane-bound particles. Apoptosis can be triggered by, for example, treatment with compounds such as etoposide, staurosporine, tumor necrosis factor-α, ceramide, and the like, or by conditions such as x-irradiation.

"About" in reference to a numerical value means ±5% of the indicated value. For example, with specific reference to the $NH_2$-terminal polypeptide derivative of PARP, produced in cells undergoing apoptosis, the molecular weight as determined using Western blot under conditions based upon detection with antibodies disclosed herein, is between 30 and 31 kDa, i.e., about 30 kDa. (30±5%=a range of between 28.5 and 31.5.)

"Apoptosis-generated protein fragment-specific antibody" refers to an antibody that recognizes apoptosis-generated protein fragments but not intact proteins.

"SEQ ID NO: 1" refers to the amino acid sequence GDEVD (Gly-Asp-Glu-Val-Asp).

"SEQ ID NO:2" refers to the amino acid sequence CKGDEVD (Cys-Lys-Gly-Asp-Glu-Val-Asp).

"Substantially pure" describes a compound which has been separated from other components which naturally accompany it. Typically, a compound is substantially pure when at least 75%, more preferably at least 90%, and most preferably at least 99%, of the total material (by volume, by wet or dry weight, or by mole percent or mole fraction) in a sample is the compound of interest. Purity can be measured by any appropriate method, e.g., in the case of polypeptides by column chromatography, polyacrylamide gel electrophoresis, or HPLC analysis. In particular, a protein is substantially purified when it is separated from the native contaminants which accompany it in its natural state.

The terms "reacts selectively" or "binds specifically" describe an antibody that recognizes and binds to target protein fragments, but does not substantially recognize and bind to other molecules, such as intact proteins.

"Etoposide" means a semisynthetic derivative of podophyllotoxin, used as an antineoplastic.

"Antineoplastic" means inhibiting the maturation and proliferation of malignant cells.

"Epitope" means a site on the surface of an antigen molecule to which a single antibody molecule binds.

"Vehicle" refers to a relatively inert substance added to a bioactive agent in order to confer a suitable consistency or form to the agent.

The present invention is directed, in part, to improved methods for the detection of cell apoptosis. Embodiments of the present invention involve contacting a sample with an antibody which binds selectively to protein fragments generated during apoptosis. By immunoassay, the amount of the antibody which becomes bound to the target protein fragments is determined, using as comparison a sample known to be free of apoptosis.

Poly-ADP-ribose polymerase (PARP) is one of the proteins whose proteolytic degradation is stimulated in a variety of cells undergoing apoptosis (Kaufmann et al., ibid.; Lazebnik et al., Nature 371:346–347 1994; Tewari et al., ibid.). As shown schematically in FIG. 1, in apoptotic cells the approximately 115 kDa PARP is preferentially cleaved at a single site, generating an $NH_2$-terminal fragment of about 30 kDa and a COOH-terminal derivative of approximately 85 kDa (apparent molecular weights as determined by SDS polyacrylamide gel electrophoresis; Kaufmann et al., ibid;

Lazebnik et al., ibid.). The five residues immediately NH$_2$-terminal to the cleavage site are completely conserved in PARP from several vertebrate species, whereas the residues immediately COOH-terminal to the cleavage site are divergent (Cherney et al., Proc. Natl. Acad. Sci. USA 84:8370–8374 1987; Saito et al., Gene 90:249–254 1990; Huppi et al., Nuc. Acids Res. 17:3387–3401 1989; Ittel et al., Gene 102:157–164 1991; Lazebnik et al., ibid.).

Additional peptide fragments are produced in cells undergoing apoptosis. For example, DNA replication complex C, DNA-dependent protein kinase, protein kinase of presenilin 1 and 2, spectrin (fodrin), as well as other polypeptides, are known to be degraded and generate peptide fragments during apoptosis. Antibodies to the peptide fragments of these polypeptides could be prepared in order to identify cells undergoing apoptosis.

We hypothesized that the highly conserved pentapeptide sequence may be critical for recognition by the protease(s) activated during apoptosis—i.e., be the apoptosis cleavage recognition site—and an antibody raised to this sequence might react selectively with the about 30 kDa NH2-terminal derivative of PARP produced in cells undergoing apoptosis (FIG. 1). Should the sequence be inaccessible in the intact PARP, or in different PARP derivatives formed during the normal turnover of the protein, then an antibody to the sequence may be expected to be a highly specific probe for apoptotic proteolysis of PARP. Conceivably, the antibody might also react selectively with fragments of proteins other than PARP that also contain the particular sequence and, therefore, may exhibit enhanced degradation during apoptosis.

We disclose herein antibodies which preferentially bind to protein fragments produced during apoptosis and, thus, confirm our hypothesis concerning the apoptosis cleavage recognition site.

Measurement of apoptosis-associated proteolysis levels can be carried out by the use of an immunoassay which allows detection of binding between apoptosis-generated protein fragments and an antibody specific to apoptosis-generated protein fragments. The amount of bound antibody can be determined by detection of enzymic, chromogenic, radioactive, fluorescent or luminescent labels which are attached to either the antibody which binds to the apoptosis-generated protein fragments or to a secondary antibody which recognizes the antibody which binds to the apoptosis-generated protein fragments.

It is preferred that antibodies for use in the methods of the present invention react selectively with apoptosis-generated protein fragments, and that they do not react with intact protein. An important feature of the present invention is an antibody prepared against the peptide CKGDEVD (SEQ ID NO: 2) that reacts preferentially with the about 30 kDa NH$_2$-terminal polypeptide derivative of poly(ADP-ribose) polymerase (PARP) produced in cells undergoing apoptosis. This antibody also reacts selectively with fragments of proteins other than PARP, i.e. the approximately 46 and approximately 35 kDa polypeptides in apoptotic PC12 cells. However, although different proteins may be degraded in apoptotic cells of different sources, thus generating reactive protein fragments of different size, if the protein fragments contain the COOH-terminal sequence GDEVD (SEQ ID NO: 1), they will be detected by the methods of this invention.

Substantially pure peptides having the amino acid sequences SEQ ID NO: 1 (GDEVD) and SEQ ID NO:2 (CKGDEVD) may be used in generating antibodies which bind with specificity thereto. Antibodies for the particular amino acid sequences described herein may be generated by, for example, immunizing a mammal with the appropriate peptide or peptide conjugate. Methods of generating both monoclonal and polyclonal antibodies which recognize these peptides are described in Antibodies, A Laboratory Manual, Cold Spring Harbor Laboratory Press, Cold Spring Harbor, N.Y. (1988), incorporated herein by reference.

Antibodies which specifically recognize apoptosis-generated protein fragments, but not intact proteins, can be prepared by standard immunization methods using a peptide which correspond to a sequence derived from the about 30 kDa NH$_2$-terminal fragment of PARP (GDEVD; SEQ ID NO: 1) as the immunogen. This peptide can be generated by standard methods known in the art. The NH$_2$-terminal extension of SEQ ID NO: 1 (GDEVD) utilized to make SEQ ID NO:2 (CKGDEVD) can itself be used as an immunogen. Other protein or peptide antigens which, regardless of their origins, length, or degree of homology with naturally occurring apoptosis-generated protein fragments, lead to the production of antibodies which bind specifically to the apoptosis-generated protein fragments, may also be used in the methods of the invention. However, preferred antibodies for use in the methods of the present invention are Ab127 and Ab128. In order to determine the effectiveness of antibodies for use in the methods of the present invention, the reactivities of the antibodies to normally occurring proteins and apoptosis-generated protein fragments are compared. Procedures for such comparison are exemplified herein.

The antibodies can be applied to the detection and measurement of apoptotic proteolysis, to the immunohistochemical tagging and quantification of cells undergoing apoptosis in vitro and in vivo, and to the identification of agents which stimulate or block apoptosis.

The methods of the invention can be used to diagnose cell apoptosis, and associated conditions, in a subject such as a mammal, and in particular a human subject. The methods can be used to determine whether a subject has or is at risk of developing a pathological condition.

The methods of the invention can also be used to diagnose a disease, disorder, or condition which is of either pathological or non-pathological origin including, but not limited to, chronic neurodegenerative disease, cancer, sepsis, trauma, hypoxia, anoxia, ischemia, spinal trauma, head trauma, lesions, and exposure to toxins.

The method of the present invention is also useful for identification of compounds which inhibit or stimulate (e.g., in oncology) apoptotic cell death by determining that the compounds inhibit or stimulate the formation of apoptosis-generated protein fragments. The protein fragments are detected by determining the extent of binding of an antibody prepared against the peptide sequence of SEQ ID NO:2 (CKGDEVD).

The methods of the present invention can also be used to determine the extent of activity of a candidate compound in decreasing or increasing the apoptotic activity in a mammal.

In association with the methods of the present invention, analysis may be performed on proteins obtained from lysed cells which have been separated by means of SDS-polyacrylamide gel electrophoresis ("PAGE"). The proteins are contacted with a selective antibody and analysis is performed, preferably by immunoassay, to determine the presence of protein fragments which bind to the antibody. Comparison may be made to a control consisting of proteins from similar lysed cells known to be free of apoptosis.

Immunoassays which may be used in the methods of the present invention include, but are not limited to: ELISA, cell-based ELISA, filter-binding ELISA, inhibition ELISA, Western blots, immunoprecipitation, slot or dot blot assays, immunostaining, RIA, scintillation proximity assays, fluorescent immunoassays using antibody conjugates or antigen conjugates of fluorescent substances such as fluorescein or rhodamine, Ouchterlony double diffusion analysis, and immunoassays employing an avidin-biotin or a streptavidin-biotin detection system. Modifications of the known immunoassay techniques may also be used.

It will also be understood by one skilled in the art that any of the immunoassays described above can be used to analyze a tissue sample from a live subject. Possible biological samples for this analysis include blood cells or biopsied cell or tissue samples which can be obtained by standard methods. The levels of apoptosis-generated peptide fragments in the above-described biological samples can be determined in any of the immunoassays described above employing antibodies that bind specifically to the peptide sequence GDEVD (SEQ ID NO:1). The level of apoptosis-generated peptide fragments determined in the biological sample from the subject being analyzed is compared to the level found in an unaffected patient, or in a known standard. This method may be used to diagnose degenerative conditions characterized by abnormal apoptosis. An increase in apoptosis-generated peptide fragments of preferably 50 percent, and more preferably 150 percent, compared to control samples, may be considered indicative of a degenerative condition.

The above-described diagnostic assays can be facilitated by the use of kits which contain the reagents required for carrying out the assays.

The present invention provides kits which may be used in the detection of cell apoptosis and in the diagnosis of diseases associated therewith. One such kit comprises: (1) a primary antibody capable of binding to protein fragments generated during apoptosis, (2) a secondary antibody conjugated to a signal-producing label, the secondary antibody being one which binds to the primary antibody; and (3) a signal-producing tertiary reagent capable of recognizing a tagged secondary antibody.

Another kit that is useful for detection of apoptosis-generated protein fragments according to the present invention includes (1) a first antibody capable of binding to protein fragments generated during apoptosis; and (2) a second antibody conjugated to a signal-producing label, the second antibody also being reactive with an apoptosis-generated protein fragment, but one that binds to a site different from that to which the first antibody binds. This kit is most suitable for carrying out a one or two-antibody immunoassay, e.g., a sandwich ELISA.

In the assay kits provided according to the present invention, the signal-producing label linked to the secondary antibody may be, for example, an enzyme, such as horseradish peroxidase or alkaline phosphatase. Preferably, both the enzyme and the substrate are provided in the kit. The kit may also include an uncoated support onto which a sample to be assayed, or the first antibody, can be immobilized.

The present invention is further described in the following examples. These examples are provided for illustrative purposes only, and are not intended to limit the methods and compositions of the present invention. Other suitable modifications and adaptations of the variety of conditions and parameters normally encountered in immunodiagnostics, apparent to those skilled in the art, are within the scope of the present invention.

EXAMPLES

Example 1

Preparation Of Antibodies Which React Selectively With Protein Fragments Generated During Apoptosis Antibodies were prepared by immunizing rabbits with an immunogen comprising the pentapeptide GDEVD (SEQ ID NO: 1) and keyhole limpet hemocyanin (KLH). The pentapeptide was directionally conjugated to KLH through $NH_2$-terminal cysteine-lysine residues (Harlow and Lane (1998) *Antibodies*, Cold Spring Harbor Laboratory, New York, incorporated herein by reference), i.e., as the heptapeptide CKGDEVD (SEQ ID NO:2). The heptapeptide was synthesized by standard solid phase methods, and its structure confirmed by fast atom bombardment-mass spectrometry. It was conjugated to KLH using maleimidobenzoyl-N-hydroxysuccinimide ester (Calbiochem, San Diego, Calif.). Two rabbits were immunized with the immunogen, and the resultant antisera were collected by standard techniques. The antisera are referred to as Ab127 and Ab128.

Example 2

Immunoblotting For Detection Of Apoptosis-Associated Proteolysis In HL60 Cells And Evaluation Of Reactivity Of Ab127 or Ab128 With Apoptosis-Associated About 30 kDa PARP Fragment HL60 cells (obtained from the American Type Culture Collection, Rockville, Md.) were cultured using published techniques (Collins et al., Nature, 270:347–349 (1977), incorporated herein by reference). Cultures of cells were incubated with either 17 micromolar etoposide (from a 1000× stock solution made in dimethylsulfoxide) to trigger apoptosis or a vehicle. After either 2 or 4 hours, cells were lysed in ice cold 25 millimolar (mM) HEPES (pH 7.5), 5 mM $MgCl_2$, 0.1% Triton X-100 and a cocktail of protease inhibitors (1 mM EGTA, 10 micrograms per ml of aprotinin, 10 micrograms per ml of leupeptin, 7 micrograms per ml of pepstatin A, 1 mM phenylmethylsulfonylfluoride (PMSF). The resulting cell lysates were subjected to SDS-polyacrylamide gel electrophoresis on 4–20% Tris-glycine gradient gels, and the separated proteins transferred to nitrocellulose membranes by Western blotting. The blots were immunostained with Ab127 (⅕,₀₀₀) followed by incubation with alkaline phosphatase conjugated goat anti-rabbit IgG (Bio-Rad, Burlingame, Calif.) and visualized as described previously (Roberts-Lewis et al., J. Neurosci. 14:3934–3944 (1994), incorporated herein by reference).

As shown in FIG. 2, the antibody labeled three polypeptides in the HL60 extracts. Two of the polypeptides were of approximately 100 and approximately 80 kDa molecular weight, and were labeled irrespective of cell treatment, although levels of the approximately 80 kDa polypeptide increased in apoptotic cells. Additionally, Ab127 labeled an about 30 kDa polypeptide which was readily detected only in etoposide-treated, but not in vehicle-treated, cells. The level of the about 30 kDa immunoreactive polypeptide increased with increasing time of cell exposure to etoposide. Stated differently, the antibodies utilized herein did not bind with the approximately 100 kDa polypeptide or the approximately 100 kDa polypeptide to the exclusion of the PARP polypeptide of about 30 kDa.

To control for the specificity of antibody reactivity, preimmune sera and immune sera that were preabsorbed with an excess of the peptide immunogen were also examined. Preimmune sera from the two rabbits did not label the about 30 kDa polypeptide. For preabsorption, Ab127 serum was diluted 50-fold in Tris-buffered saline (pH 7.4), and divided into two aliquots. The peptide CKGDEVD was added to one aliquot at 300 micrograms/ml, and the two aliquots were incubated at room temperature for 1 hour. Next, each aliquot was diluted 100-fold and used for immunoblotting. As shown in FIG. 3, immunolabeling of the about 30 kDa polypeptide was blocked by Ab 127 preabsorption.

Example 3

Confirmation That The About 30 kDa Immunoreactive Polypeptide Is A Protein Fragment Generated During Apoptosis Nuclear extracts of HL60 cells were treated with an enzymatically active preparation of the ICE-like protease CPP32. The baculovirus expression system was used to produce rhCPP32 (Meyer et at., Neurosci. Abstr. 22:565 (1996), incorporated herein by reference) and was demonstrated to be proteolytically active based on cleavage of a synthetic peptide substrate (method described in Nicholson et al., Nature 376:37–43 (1995), incorporated herein by reference). The protease was purified to ~95% homogeneity by chromatography on a Q-Sepharose FF anion exchange resin. Nuclear extracts were treated with catalytic amounts of the partially purified rhCPP32 and incubated at 23° C. for up to 60 minutes. As shown in FIG. 3, incubation with rhCPP32 resulted in an increase in the level of an Ab127 immunoreactive about 30 kDa polypeptide (lane 2). The labeled polypeptide precisely co-migrated with the immunoreactive about 30 kDa polypeptide extracted from intact HL60 cells undergoing apoptosis (lane 1). Preabsorption of the antibody with the peptide CKGDEVD eliminated reactivity with the about 30 kDa polypeptide. The results indicate that the apoptosis-associated degradation of PARP can be specifically detected by an antibody directed at the GDEVD cleavage locus at the COOH-terminus of the about 30 kDa fragment.

Example 4

Use Of Immunoblotting To Detect Apoptotic Proteolysis In Neuron-Like Cells

The cell line PC12 differentiates into a sympathetic neuron-like cell in response to nerve growth factor (NGF), and dies by apoptosis following NGF deprivation (Batistatou et al. (1993) J. Neurosci. 13, 4433–4438). A protease inhibitor of the ICE family has been found to reduce the NGF-deprivation induced apoptosis (Troy et al. (1996) Proc. Natl. Acad. Sci. 93, 5635–5640). Accordingly, reactivity of Ab127 and Ab128 with polypeptides was compared in NGF-maintained PC12 cells and NGF-deprived apoptotic PC12 cells.

PC12 cells were maintained in NGF-containing medium under low serum conditions (0.18% fetal bovine serum) for 7 days. NGF withdrawal was initiated by three washes with NGF-free culture medium, followed by addition of a neutralizing antibody to NGF (Boehringer Mannheim, Indianapolis, Ind.). After various time intervals following NGF deprivation, apoptotic cell death was evaluated by measurements of cell survival, internucleosomal DNA fragmentation, and chromatin condensation. Immunoblotting with Ab127 (FIG. 4) or Ab128 (data not shown) was performed as described in Example 2 above, and demonstrated that, by 8 hours following NGF deprivation, two immunoreactive polypeptides of approximately 46 and approximately 35 kDa appeared in the cells deprived of NGF (FIG. 4). The content of these polypeptides increased with longer periods of NGF deprivation.

Example 5

Confirmation That The Approximately 46 And Approximately 35 kDa Immunoreactive Polypeptides Are Protein Fragments Generated During Apoptosis Cell-free nuclear extracts of PC12 were incubated with recombinant human CPP32, the ICE-like protease as described in Example 3 for HL60 cell extracts. Incubation of nuclear extracts of PC12 cells with CPP32 led to a time-dependent increase in the content of approximately 46 and approximately 35 kDa polypeptides which co-migrated with two immunoreactive species obtained from NGF-differentiated PC12 cells deprived of NGF (FIG. 4). Migration of the two polypeptides is distinguishable from the immunoreactive about 30 kDa PARP fragment in apoptotic HL60 cells. The results indicate that the approximately 46 and approximately 35 kDa polypeptides represent fragments from proteins other than PARP that contain the GDEVD domain at their COOH-terminus and are specifically generated in PC12 cells undergoing apoptosis. It will be recognized by one skilled in the art that Ab127 or Ab128 may be used for affinity purification of these ICE-like protease substrates and their identification by protein microsequencing or mass spectrometry methods.

Example 6

Immunohistochemical Detection Of Cell Death By Apoptosis

NGF-differentiated PC12 cells were grown on chambered microscope slides which had been pre-treated with poly-ornithine and laminin. After 7 days, the culture medium was changed and half of the cultures were deprived of NGF as described in Example 4. After 24 hours, cells were processed for immunohistochemistry using Ab127 as follows. Cells were fixed in 2% paraformaldehyde in 0.1 M sodium phosphate buffer, pH 7.4 (60 minutes), and incubated sequentially in 0.09% $H_2O_2$ in phosphate buffer (20 minutes), followed by 10% normal goat serum/0.5% Triton X-100/Tris-buffered saline (TBS) for 60 minutes. Cultures were incubated in TBS alone or TBS containing Ab127 at dilutions from 1/10,000 to 1/40,000 for 2 hours. Following 3 washes in TBS, all cultures were incubated in biotinylated anti-rabbit IgG (Vector, Burlingame, Calif.) diluted 1/200 in TBS. After 30 minutes, the cultures were washed in TBS and incubated with the avidin-biotin-peroxidase complex (ABC Elite kit, Vector) according to the manufacturer's instructions. Following several washes in TBS, color development was carried out using a standard nickel intensified diaminobenzidine method. After rinsing, cultures of cells were placed under cover slips and photomicrographs were taken using a Nikon Microphot system.

Figure 5A:
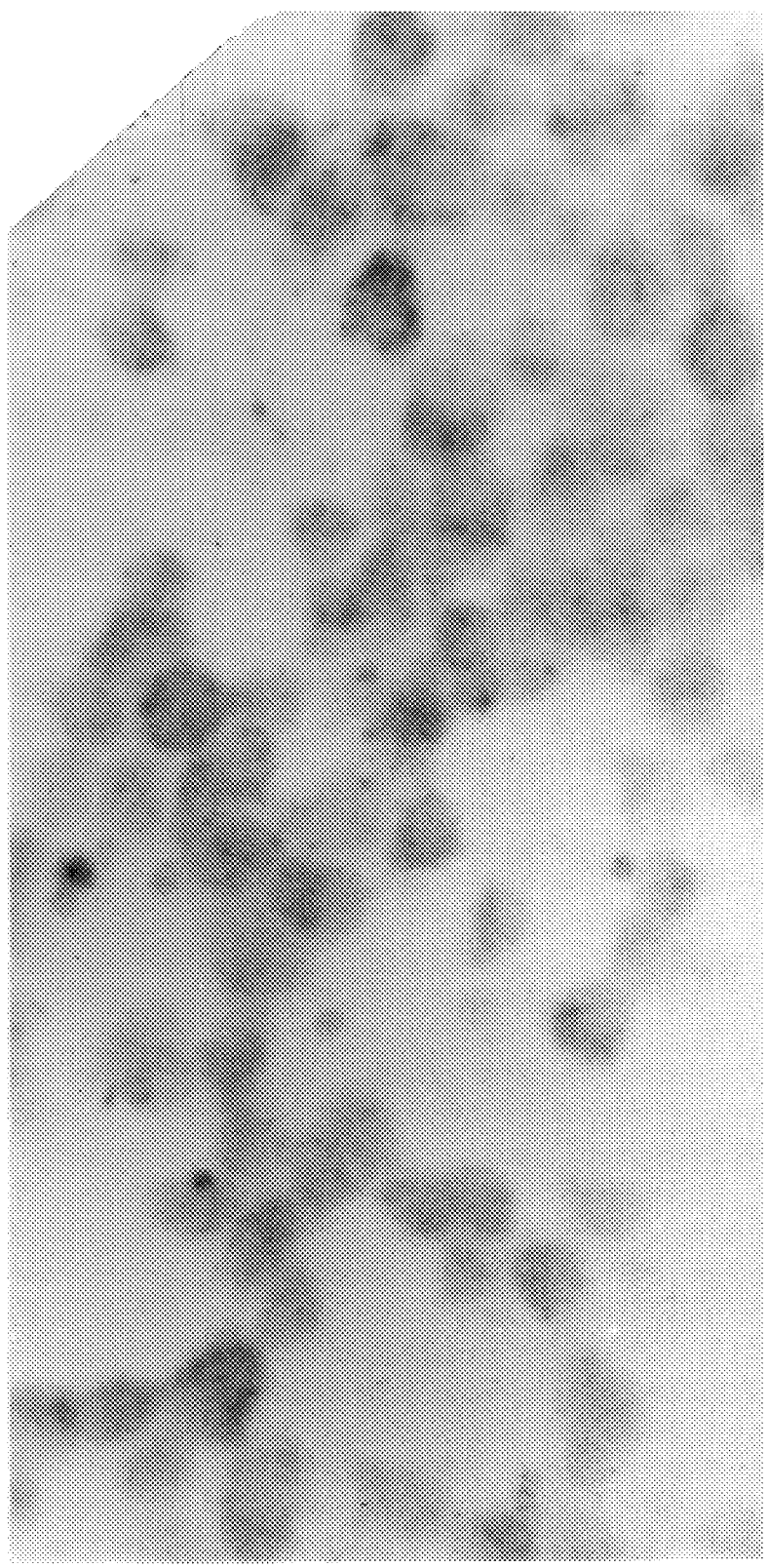
FIGS. 5A and 5B show immunohistochemical detection of apoptotic proteolysis in growth factor-deprived neuronally differentiated PC12 cells. PC12 cells either maintained on NGF (5A) or withdrawn from NGF for 24 hours (5B) were labeled with Ab127 at 1/20,000 using a standard indirect immunoperoxidase technique (e.g., Roberts-Lewis et al. (1994) ibid.) Cells were photographed at 200× magnification, 1260× magnification for the insert. Note that Ab127 strongly labels a subset of NGF-deprived cells. The immunostaining took the form of a series of small, intensely labeled puncta which sometimes formed an annulus around the cell. No immunolabeling of NGF-deprived PC12 cells was observed in the absence of Ab127 (data not shown).
Figure 5B:
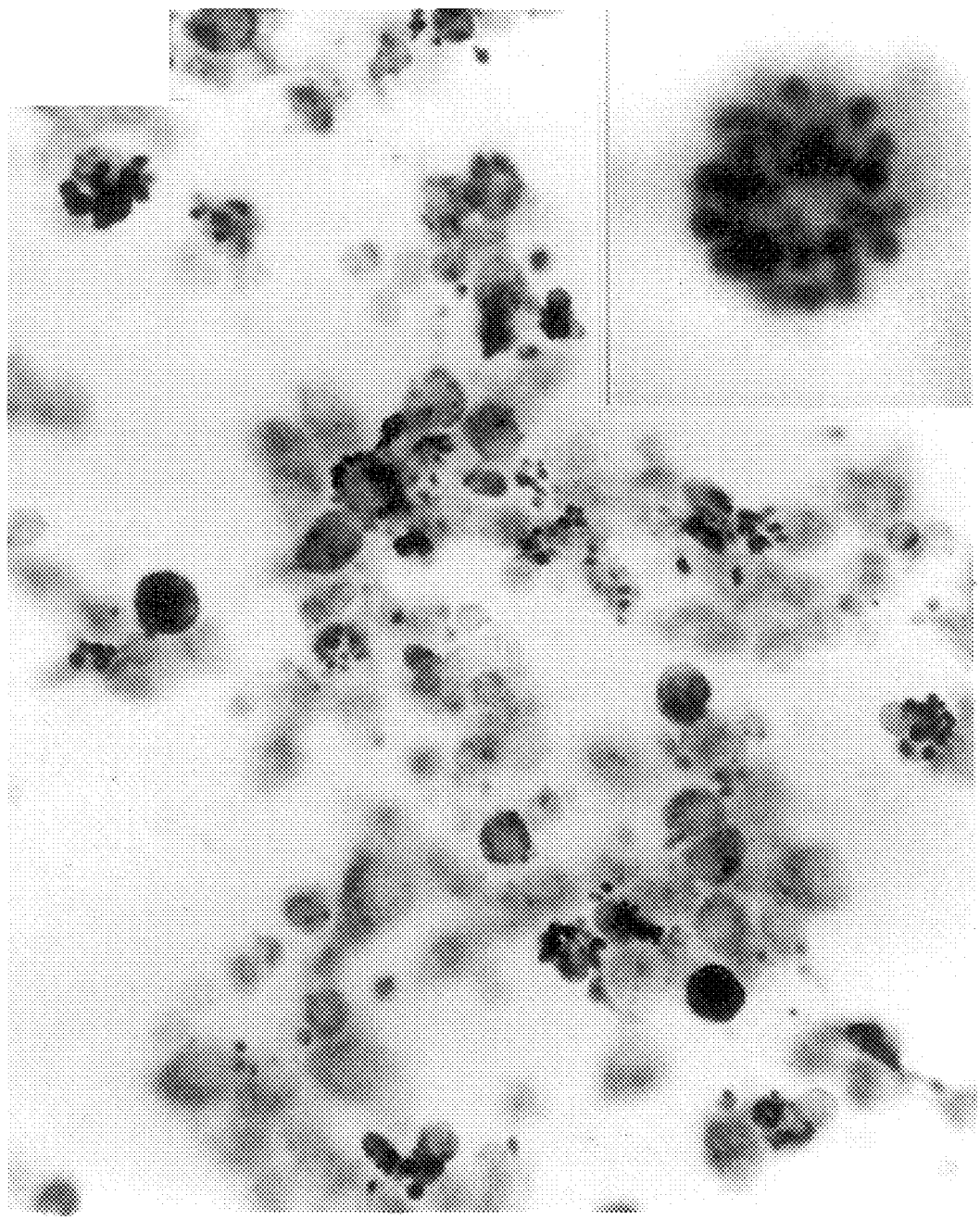

As shown in FIG. 5, only very light background staining was observed for Abb 127-stained PC12 cells maintained on NGF (FIG. 5A). Thus, Ab127 did not react with proteins in healthy PC12 cells that were maintained on NGF. NGF-deprived cells labeled in the absence of the Ab127 primary antibody showed no immunoreactivity. In NGF-deprived cultures, many cells did not label with Ab127 above background, but a subset of cells was intensely immunolabeled (FIG. 5B). This specific staining was only observed with Ab127 treatment, and took the form of clusters of darkly stained puncta, which often appeared to form a ring (FIG. 5B, insert). The pattern of immunolabeling is similar to the appearance of apoptotic bodies forming from the disintegration of the plasma and nuclear membranes in cells undergoing apoptosis.

Similar results were obtained with other cells. Hippocampal neurons grown in primary culture were stimulated to die by application of the neurotoxic metabolic poison 3-nitropropionic acid. Independent labeling of the cultures with the nuclear stain Hoechst 33258 revealed the presence of apoptotic neurons, with condensed chromatin fragmenting into apoptotic bodies, in the midst of viable cells. When the cultures were immunostained with Ab127, most of the cells were not labeled, but a subset of neurons was intensely immunoreactive. In contrast, no Ab127 immunoreactive cells were found in control cultures that had not been treated with the neurotoxin.

Example 7

Immunohistochemical Labeling Of Apoptosis-Associated Proteolysis In Developing Rat Brain To examine the use of Ab127 as a probe for identifying cells undergoing apoptosis in situ, Ab127 immunohistochemistry was performed on neonatal rats. It has been shown that excess numbers of neurons are formed during early rat brain development, and significant programmed neuronal death occurs by apoptosis during the first 2 post-natal weeks (reviewed in Oppenheim (1991) Annu. Rev. Neurosci. 14, 453–501). To examine the utility of Ab127 in identifying cells undergoing apoptosis in situ, Ab127 immunohistochemistry was performed on neonatal rats.

Brains of rats 1, 4, 7 and 9 days of age were fixed in 4% paraformaldehyde, cryoprotected, sectioned in the sagittal plane at 40 micrometers on a sliding microtome, and stained for Ab127 immunoreactivity using a standard indirect immunoperoxidase procedure (described in, e.g., Roberts-Lewis et al., J. Neurosci. 14:3934–3944 (1994), incorporated herein by reference). The Ab127 was used at dilutions ranging from 1/1,000 to 1/50,000. Control sections were processed as described in Roberts-Lewis et a., above, except that the primary antibody (Ab127) was omitted. Following immunostaining, sections were mounted onto glass slides, dehydrated, delipidated, placed under cover slips, and examined and photographed using a Nikon Microphot system.

The immunostaining with Ab127 of the developing rat brain revealed a highly restricted distribution of intensely immunoreactive cells. Nearly all brain cells during the first 10 post-natal days were devoid of Ab127 immunoreactivity. However, groups of cells within specific brain regions and at particular developmental stages were heavily immunopositive.

Figure 6A:
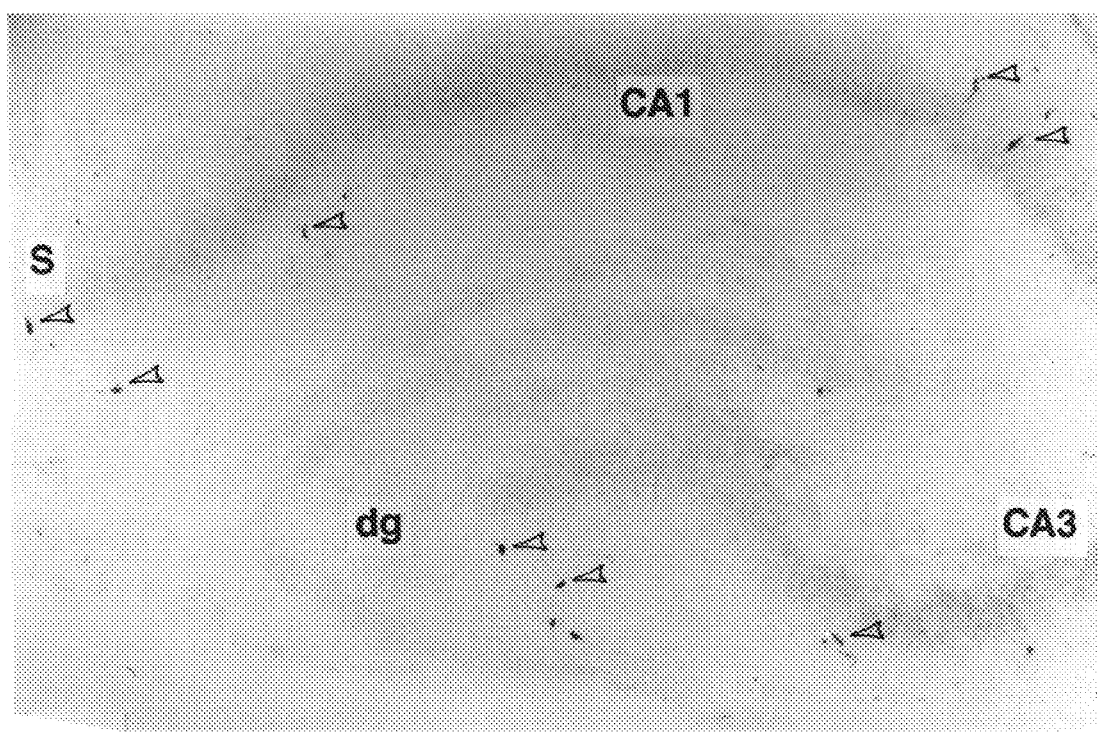
FIGS. 6A–6C show immunohistochemical detection of apoptotic proteolysis in the developing post-natal rat brain. Sagittal sections from aldehyde-fixed rat brain were prepared at 40 µm on a freezing microtome, and were labeled with Ab127 (1/3,000) using a standard indirect immunoperoxidase technique (Roberts-Lewis et al. (1994) ibid.) A—Hippocampal formation, post-natal day 4 (100× magnification); DG—dentate gyrus; CA3—the CA3 subfield of hippocampus; CA1—the CA1 subfield of hippocampus; S—subiculum. Note the scattered, intensely immunoreactive cells (open arrowheads). At higher magnification, these cells have the morphology of neurons. B—Inferior colliculus, post-natal day 9 (200× magnification). Scattered neurons exhibit intense immunoreactivity in their perikarya and dendritic processes. Note the beaded appearance of the immunolabeled dendrites, indicative of active degeneration. C—Parietal neocortex, post-natal day 9 (100× magnification). Immunoreactivity indicative of apoptotic proteolysis is restricted to a small subset of neurons in layer 2.
Figure 6B:
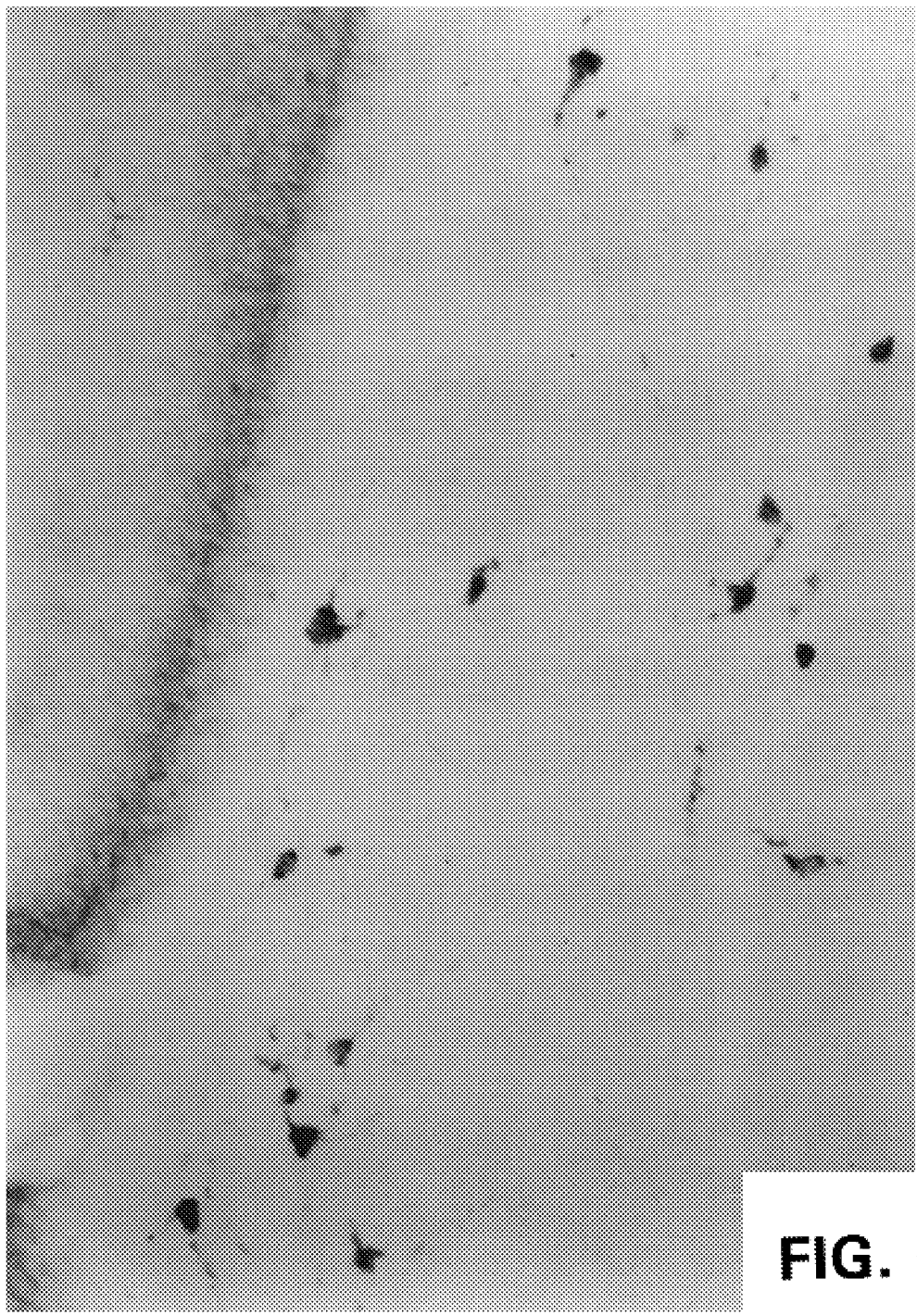
Figure 6C:

FIG. 6 shows the immunolabeling of subsets of cells in the parietal cortex, hippocampal formation, and inferior colliculus. As shown in FIG. 6A, the post-natal day 4 hippocampus contains intensely immunoreactive cells scattered among several subfields. FIG. 6B illustrates the heavy immunostaining of neurons of the inferior colliculus at post-natal day 9. The neurons are in an acute stage of degeneration, as manifested by the beaded, fragmented appearance of their dendrites. As shown in FIG. 6C, only rare neocortical cells were immunoreactive. In parietal cortex, scattered neurons at an acute stage of degeneration were labeled, almost exclusively in layer 2. At a later stage of development, fewer immunopositive neurons were detected in the neocortex, hippocampus, and other brain regions, consistent with these neurons having the short residence time characteristic for cells dying by apoptosis. However, by post-natal day 9, numerous intense immunopositive cells appeared in the corpus callosum. Their location and morphology identify the immunolabeled cells as oligodendroglia.

No immunolabeling was observed in either neurons or oligodendrocytes in sections stained in the absence of Ab127. The results confirm and extend the observations reported above for cultured cells, and indicate that an antibody directed at the preferred ICE-homolog proteolytic cleavage site GDEVD may be used to selectively label cells undergoing developmental apoptosis in situ.

All references cited herein are hereby incorporated by reference in their entireties.

What is claimed is:

1. A method of detecting apoptosis in cells comprising the steps of: (a) contacting a sample of cells with an antibody which binds specifically to protein fragments generated during apoptosis, wherein said antibody binds specifically to an epitope on said protein fragments comprising an amino acid sequence selected from the group consisting of SEQ ID NO: 1 and SEQ ID NO:2; (b) determining by immunoassay the amount of said antibody which binds to said sample; and (c) comparing the amount of antibody bound in step (b) with the amount of said antibody which binds to a sample known to be free of apoptosis, wherein if said amount in step (b) is greater than said amount in said sample known to be free of apoptosis, then apoptosis is detected.

2. A method of detecting apoptosis in cells or tissue in situ comprising the steps of: (a) contacting a fixed preparation of said cells or tissue with an antibody which binds specifically to protein fragments generated during apoptosis, wherein said antibody binds specifically to an epitope on said protein fragments comprising an amino acid sequence selected from group consisting of SEQ ID NO: 1 and SEQ ID NO:2; (b) determining by immunohistochemical analysis the amount of said antibody which binds to said preparation; and (c) comparing the amount of antibody bound in step (b) with the amount of said antibody bound to a fixed preparation of cells or tissue not undergoing apoptosis, wherein if said amount in step (b) is greater than said amount in said cells or tissue not undergoing apoptosis, then apoptosis is detected.

3. The method of claim 1 or 2 wherein said protein fragments are produced from poly-ADP-ribose polymerase.

4. The method of claim 3 wherein said protein fragments are $NH_2$-terminal fragments of about 30 kDa.

* * * * *